Figure 1:
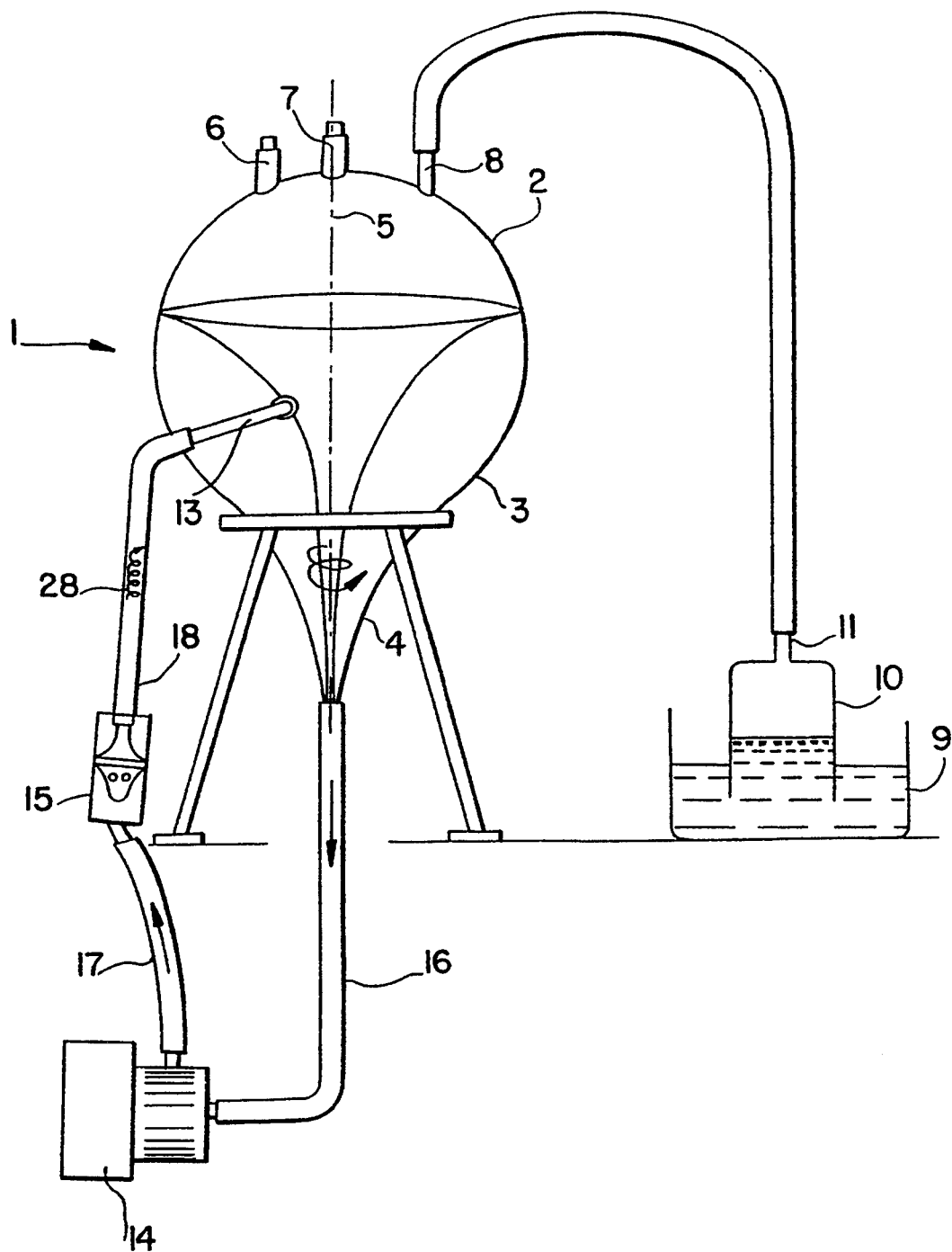

United States Patent [19]
Ott, deceased et al.

[11] Patent Number: 5,391,328
[45] Date of Patent: Feb. 21, 1995

[54] APPARATUS FOR INTRODUCING AND BONDING GAS INTO WATER

[75] Inventors: Walter Ott, deceased, late of Stäfa, Switzerland; Peter Kolia, Pécs; Michael Lantos, Budapest, both of Hungary; Jürg Kehrli, Jona, Switzerland

[73] Assignee: Tecno-Bio Co., Ltd., Tokyo, Japan

[21] Appl. No.: 212,680

[22] Filed: Mar. 11, 1994

Related U.S. Application Data

[60] Continuation of Ser. No. 957,395, Apr. 22, 1993, abandoned, which is a division of Ser. No. 348,010, Aug. 23, 1989, abandoned.

[30] Foreign Application Priority Data

Oct. 23, 1987 [DE] Germany .................. 87115583
Sep. 30, 1988 [DE] Germany .................. 88116279

[51] Int. Cl.⁶ .................................. B01F 3/04
[52] U.S. Cl. ........................... 261/36.1; 261/76
[58] Field of Search ................... 261/76, 36.1

[56] References Cited

U.S. PATENT DOCUMENTS

| | | | |
|---|---|---|---|
| 2,057,218 | 10/1936 | Timpson | 261/76 |
| 2,570,669 | 10/1951 | Hannigan | 261/76 |
| 2,653,801 | 9/1953 | Fontein et al. | 261/76 |
| 2,812,168 | 11/1957 | Kumpman | 261/76 |
| 2,813,833 | 11/1957 | Revallier . | |
| 2,986,343 | 5/1961 | Trentini et al. . | |
| 3,246,683 | 4/1966 | Yap et al. . | |
| 3,867,195 | 2/1975 | Pfeuffer . | |
| 4,008,163 | 2/1977 | Ingels . | |
| 4,087,862 | 5/1978 | Tsien . | |
| 4,337,152 | 6/1982 | Lynch . | |
| 4,483,826 | 11/1984 | Louthan | 261/36.1 |
| 4,562,014 | 12/1985 | Johnson | 261/76 |
| 4,580,904 | 4/1986 | Hacheney . | |
| 4,761,077 | 8/1988 | Werner | 261/76 |
| 5,037,584 | 8/1991 | Toll | 261/76 |

FOREIGN PATENT DOCUMENTS

| | | |
|---|---|---|
| 030517 | 6/1981 | European Pat. Off. . |
| 134890 | 3/1985 | European Pat. Off. . |
| 263443 | 4/1988 | European Pat. Off. . |
| 3728223 | 5/1989 | European Pat. Off. . |
| 1005459 | 4/1952 | France . |
| 1642794 | 4/1971 | Germany . |
| 370057 | 6/1983 | Switzerland . |
| 8582 | of 1913 | United Kingdom . |
| 1260163 | 2/1972 | United Kingdom . |

OTHER PUBLICATIONS

"Wasser: Unsere Lebensgrundlage", Mar. 16, 1992.
"Wilfried Hacheney's Levitiertes Wasser" Technolgien des Zukunft, pp. 3–9, Apr. 1991.
Betrieb Markte Technik, Feb. 29, 1980.
Verbrauchen #298, Dec. 23, 1986.

*Primary Examiner*—Tim Miles
*Attorney, Agent, or Firm*—Michael N. Meller

[57] ABSTRACT

A method for introducing gas like oxygen, air or carbon dioxide into water, in which a water flow enriched in the gas is passed through a reaction chamber so that the flow rotates around and moves along the Longitudinal axis, a sudden pressure minimum is provided in a section of this axis where gas comprised in the flow gets collected and mixed with vapor, the pressure is increased after the minimum, whereby gas is swallowed by water so that gas molecules get bound to water molecules. The apparatus for carrying out the method comprises a closed recirculating path with the reaction chamber, the flow is maintained by a pump, and the gas is introduced in the water either by a vortex stream or by a water jet pump. The so obtained water comprises the gas in stable and bound state in a concentration exceeding normal saturation. The dielectric constant and certain physical parameters of such water differ from those of pure water.

9 Claims, 14 Drawing Sheets

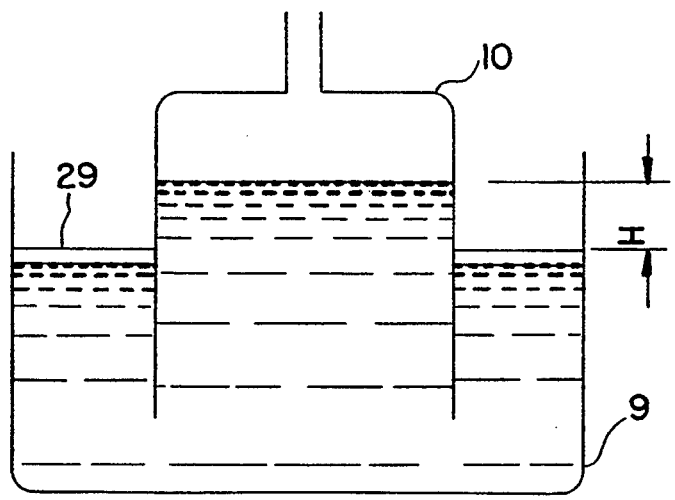
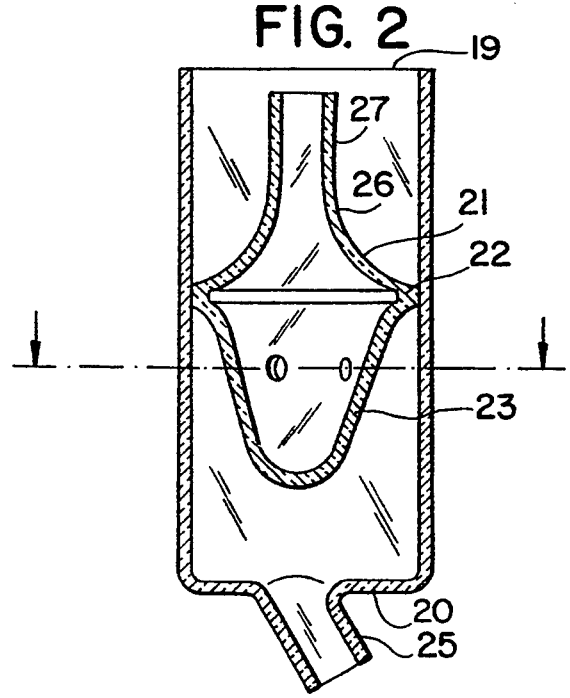
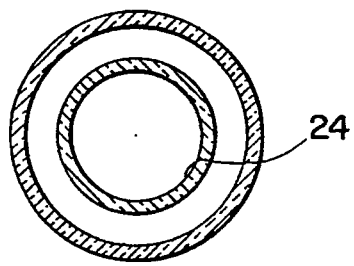

APPARATUS FOR INTRODUCING AND BONDING GAS INTO WATER

This is continuation of U.S. Ser. No. 07/957,395, Apr. 22, 1993, now abandoned, which was a divisional application of U.S. Ser. No. 07/348,010, filed Aug. 23, 1989, now abandoned, which, in turn, is a continuation of International application PCT/EP88/00948, filed Oct. 1, 1988.

The invention relates to a method for introducing a predetermined gas or gas mixture into water in a specific way which differs from the one which leads to dissolution of the gas, to an apparatus for carrying out the method and to the water containing a predetermined gas or gas mixture in a specially bound state differing from the state of said gas in water when being dissolved therein.

It is well known in the art that various gases can be dissolved in water and under any given temperature and pressure and in case of each particular gas there exists a maximum or saturation concentration which forms an upper limit for the stable presence of that gas in water. In case of oxygen such data can be found e.g. in the book entitled "Standard Methods for the Examination of Water and Waste Water" prepared and published by the American Public Health Association, Managing Editor: Mary Ann H. Frason (sixteenth edition). Chapter 421 of this book includes these tables and describes in detail how dissolved oxygen can be determined. Similar data can be found in various textbooks for physics for other gases as well.

It is also known, that water can be oversaturated by a gas if the water is intensively mixed or sprinkled under a gaseous atmosphere or if the gas is introduced therein under a higher pressure. In such cases, however, the excess amount of gas is not bound by the water in a stable condition and bubbles out of the water within a short period of time when the pressure or intensive movement has finished.

For understanding the present invention certain properties of water should be pointed out. It is well known that "simple" water, the so called monomeric $H_2O$, is built of 2 H and 1 O atoms. On the "L" path of the oxygen atom the electrons $2s^2\,2p^4$ will be complemented with the two electrons of the two hydrogen atoms to build up a configuration of 8 members i.e. in a common electron shell of 8 electrons there are located the two hydrogen nuclei and the oxygen nucleus with its $1\,s^2$ electron shell. In this way a polarized molecule with a strong covalent binding is formed, in which the collective electrons are in a sigma binding. From this configuration it follows that such electrons can easily turn around their axis of connection.

It is known that one electron binding of the $O_2$ molecule is in sigma while the other one in pi state which results in a comparatively stiff structure. This is shown e.g. in the book of L. Holics: Fizika (Physics), on page 1046, FIG. 21.1 (Müszaki Könyvkiadó, Budapest, 1986)

The monomeric water molecule is a formation with a radius of 1.33 angström, the centre thereof is occupied by the oxygen atom and the two hydrogen atoms are connected thereto with a binding angle (valence angle) of 104.45°. The distance between the H atoms is 1.63 angström and the binding energy is about 100 kcal/mol.

From these data it can be calculated that the volume of a single $H_2O$ molecule is about 11 cubic angström. If the full volume of the $H_2O$ molecule in one liter water is calculated, a value of about 370 $cm^3$ is obtained. The remaining 630 $cm^3$ is free space. This formation created the possibility that so-called hydrogen bridges be created between the oxygens and hydrogens of adjacent molecules which bridges have, of course, substantially lower energy levels. In the book of I. Tarján and Gy. Rondó: 'A biofizika alapjai' (Fundamentals of Biophysics) published by Medicina Könyvkiadó, Budapest, 1987 pp. 32–33 and 52, it is disclosed that the binding energy of the H-bridge is about 3 to 8 kcal/mol; and the binding is established between interrelated dipole molecules. Although the hydrogen is an element with a single valence value, there are a number of compounds, in which hydrogen is connected to two atoms. Such binding occurs mainly if hydrogen is connected to fluor, oxygen and nitrogen atoms.

In the $H_2O$ molecule the distance of the covalent binding between the oxygen and the hydrogen is 1 angström, while in the hydrogen bridge the oxygen to hydrogen distance is 1.76 angström.

From the monomeric water a "polymeric" phase is formed by means of the hydrogen bridges, in which the weak hydrogen bridge bindings and the desorientation due to thermal movement form a liquid crystal structure which has respective statistical probability (distribution) at any given temperature. The number of the water molecules that form the polymeric phase and the volume of the respective clusters that can be regarded as polymers both depend from the temperature. This hypothesis has been verified by the X-ray diffraction examinations described in the book of D. Eisenberg and W. Kauzmann: 'The Structure and Properties of Water' (oxford Claredon Press, London 1969) and the same is summed in J. Ernst: Bevezetés a fizikába (Introduction to Physics) published by Akadémia Kiadó, Budapest 1968. It should be noted that the terms "cluster", "polymeric fraction" and "associatum" used in the literature are synonims.

Page 111. of the aforementioned book of D. Eisenberg shows the temperature dependency of the polymeric fractions (in more detailed way in chapter 4.2).

From these diagrams it can be seen that with decreasing temperature—till +4° C.—the degree of polymerization increases i.e. the structure tends to be more crystal-like. As a consequence of this phenomenon the density, the dielectric constant, the surface tension and the optical refraction of the water will be higher with decreasing temperature.

The object of the invention is to utilize these properties of water and to provide a method by which a gas or a gas mixture can be bound to water in an amount which substantially exceeds the amount soluble in water under same temperature and pressure conditions.

A further object is to provide an apparatus for carrying out the method.

According to the invention a method has been provided for introducing gas into water, in which water is passed in a path with a predetermined flow rate, a surface of the flowing water is exposed in a portion of the path to the gas under a predetermined pressure so that a fraction of the gas is taken away by the flow to obtain water enriched by the gas, wherein the flow of enriched water is passed through a reaction chamber inserted in a series connection in the path and has a central axis, the flow is caused to simultaneously rotate around and flow along the axis to form thereby a pressure decrease in radial direction towards the axis, the pressure is decreased in flow direction along the axis to reach a minimum in a short section, then the pressure is increased again to at least partially collect thereby the fraction of the gas at the section of minimum pressure and to bound at least a portion of molecules of the gas to water molecules when exposed to increased pressure past the section.

The introduction of gas will be more intensive if the path is arranged in a closed loop and the water is repeatedly recirculated.

It is often convenient if the gas is placed in a closed space that communicates with the flow path of water.

The partial pressure of the gas can be maintained if vapor is condensed from the closed gas space.

It is preferable if water is recirculated in a flow free of turbulences, since cavitation accompanying turbulences might destroy the bounds established between the gas and water molecules.

The most convenient is when the gas is kept under normal atmospheric pressure.

The effectivity of the method is higher if the water has a temperature below 23° C.

It is preferable if the temperature of water is kept constant during the process.

in an embodiment the exposed surface of the flowing water is a surface of a vortex formed in a container connected in the flow path.

In an alternative embodiment the exposed surface is a surface of a jet stream of the water at a location surrounded by the gas sucked in by vacuum provided by pressure drop concomittant with the jet stream.

It is preferable if the gas is oxygen, air or carbon dioxide. Nitrogen can also be used, since it forms the major component of air.

In most applications the recirculation is maintained until an amount of gas is bound to the water which substantially exceeds concentration corresponding to saturation of water with the same gas when being dissolved therein. The saturation should be interpreted at the pressure and at actual temperature of the recirculating water.

The result of the gas take up can be monitored if the dielectric constant of the water is measured and the recirculation is maintained until a predetermined increase in dielectric constant is reached.

The optimum flow rate can be set if prior to the inducing step gas-free water is passed through the reaction chamber and the flow rate is increased until bubbles are visible at the section of minimum pressure, then the flow rate used during the method is set to a value which is slightly below the rate at which bubbles emerged.

According to the invention an apparatus has been provided for introducing gas into water, which comprises a container storing the water and having a space above water filled with gas to be introduced, a closed path of conduits that start from and end in the container, a pump inserted in the path to recirculate water in the path, in which a reaction chamber is connected in the path, the reaction chamber has an inner space with a rotational symmetrical form that has an axis, a plurality of tangential inflow openings are provided near inflow end of the inner space to cause rotation of inflowing water around the axis, in the path of rotating flow of water in front of the openings the reaction chamber has a part with continuously tapering cross section ending in a short duct, the path has a widening portion in front of the duct, and the closed path comprises means for intensively contacting the gas with the water.

In a preferable embodiment the means for contacting the gas with water is a water jet pump with water inflow and outflow ducts connected in series in the flow path and a gas inlet duct connected to the gas space of the container.

In an alternative embodiment the means for contacting the gas with water is formed by the container that defines an inner space being circularly symmetrical relative to an axis, the container has an upper part with a substantially spherical shape, a medium part tapering in a direction away from the upper part and a narrow lower part tapering in the same direction and ending in an outflow opening, a duct is extending obliquely out of the upper portion of the medium part substantially at or just below a height in which the container has the largest diameter and closes an acute angle at least with the tangential plane of the container for introducing water and for forming a vortex in the container, the duct and the outflow opening are coupled to the closed flow path.

The effectivity can be increased if a plurality of reaction chambers are connected in parallel across the flow path.

It is preferable if the gas space in the container communicates with a gas supply means for supplying measurable quantity of gas in the space, in operation the means provides atmospheric pressure in the space.

In an advanced embodiment the reaction chamber has an inflow end portion with a hollow rotational paraboloid form, the openings are defined in the wall of the inflow end portion, an inflow duct is coupled to the flow path and a cylindrical pressure chamber is formed between the duct and outer wall of the paraboloid portion.

A preferable embodiment comprises means for condensing vapor from the gas space.

A further embodiment comprises temperature regulator means for adjusting the temperature of circulating water to a preset value.

According to the invention water can be provided by the method and the apparatus which comprises a gas in excess quantity relative to an equilibrum condition corresponding to the saturation thereof with the same gas on any predetermined temperature and pressure, this water is characterized in that the gas is contained in a stable and bound state under said predetermined temperature and pressure.

In such water the dielectric constant is distinctively higher than that of pure water.

It has also been observed that such water is more structured than pure water of the same temperature and pressure is i.e. selected physical parameters of this water correspond to similar parameters of pure water with a lower temperature.

The water made according to the invention has unique physical properties and it has, according to preliminary tests, unexpected physiological and other effects in a number of fields and applications.

Figure 5:
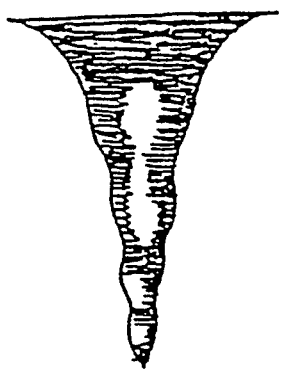
Figure 6:
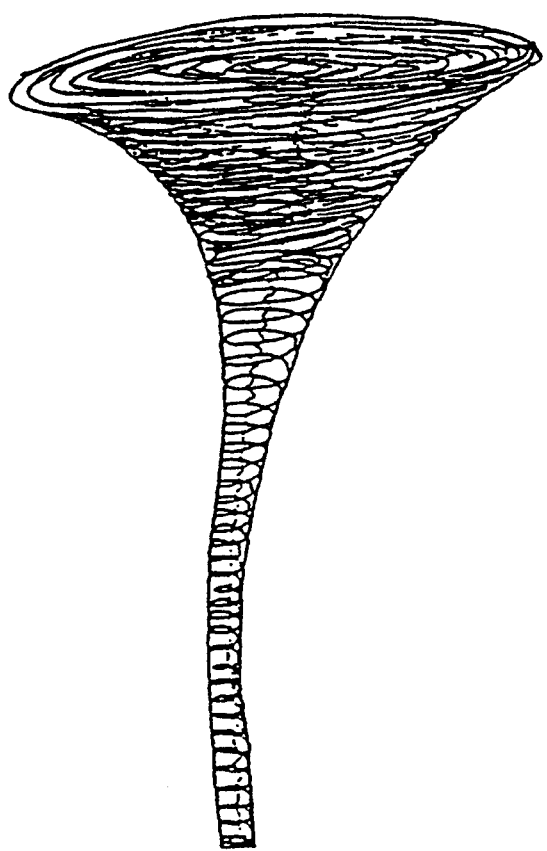
Figure 7:
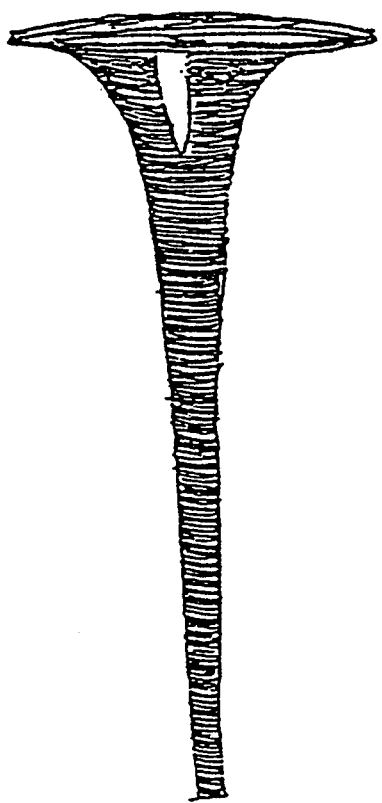
Figure 8:
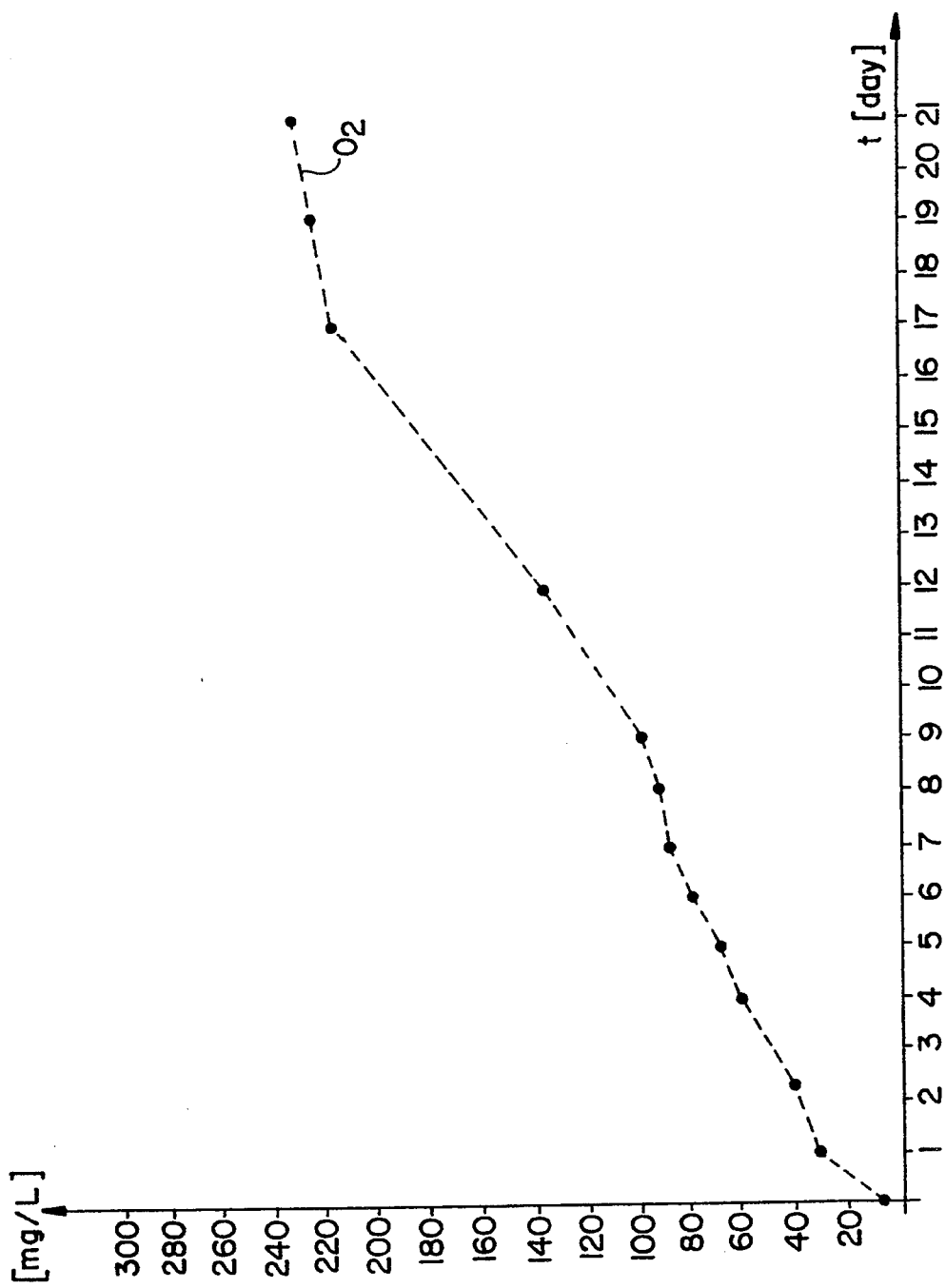
Figure 9:
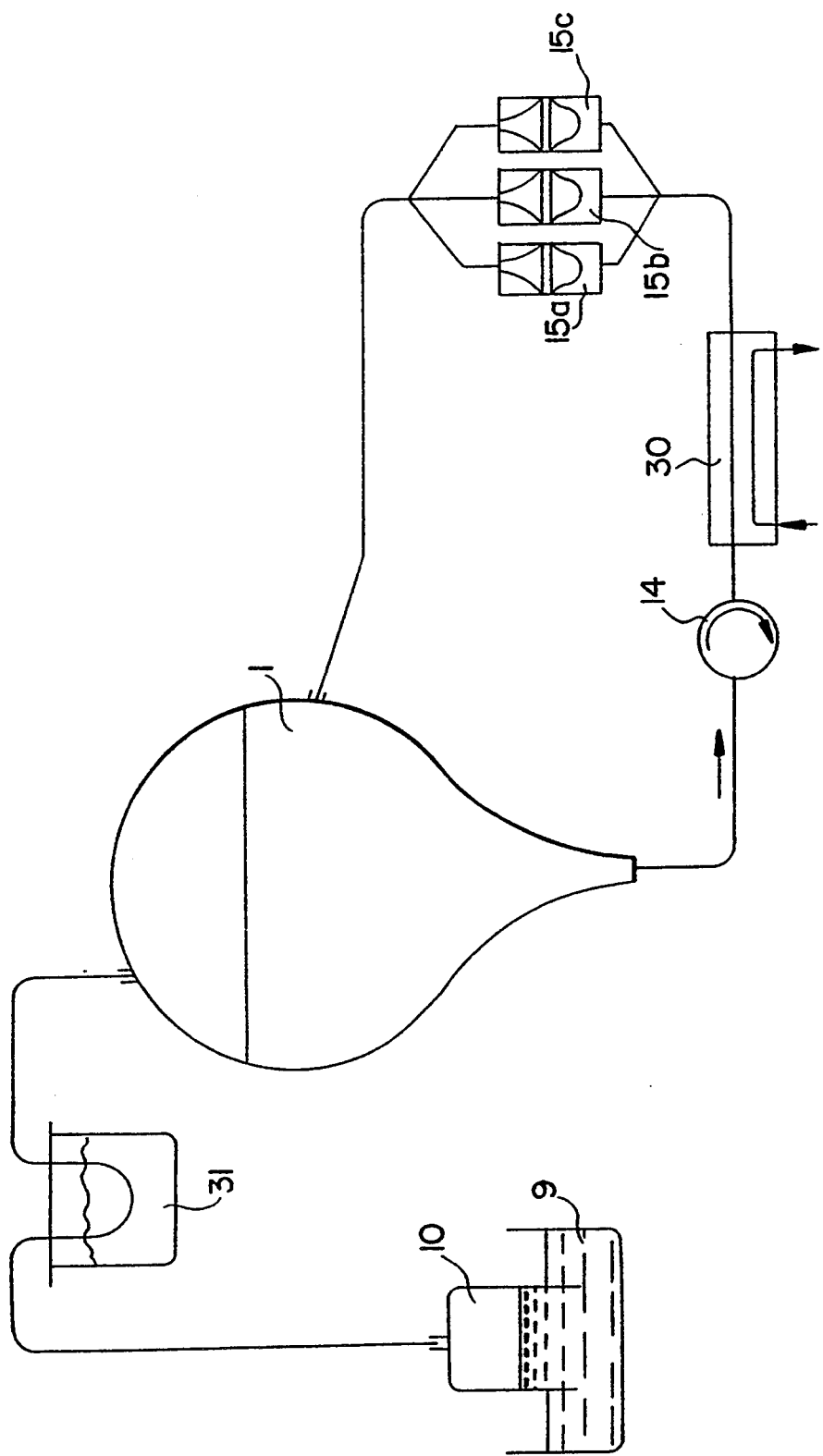
Figure 10:
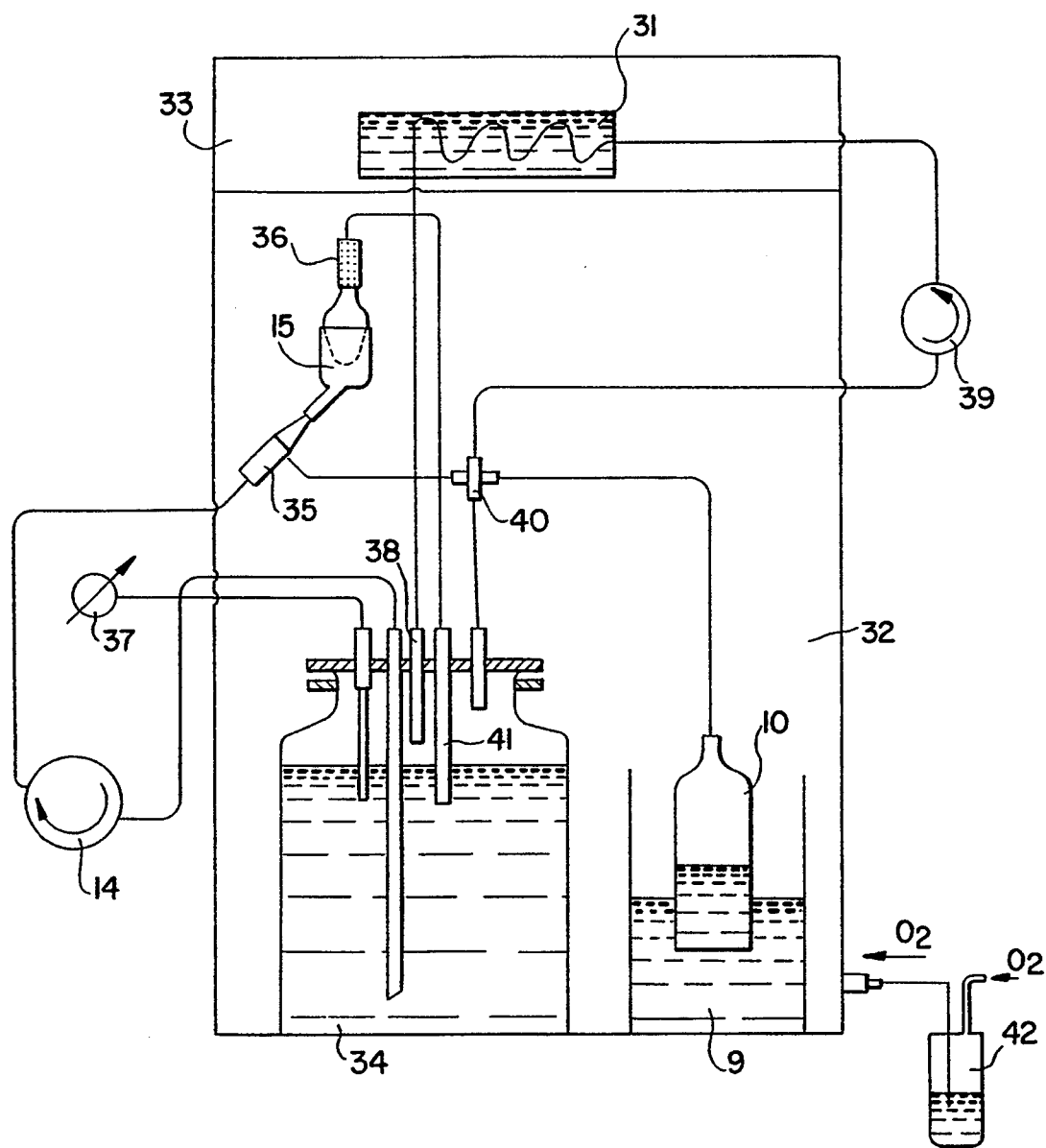
Figure 11:
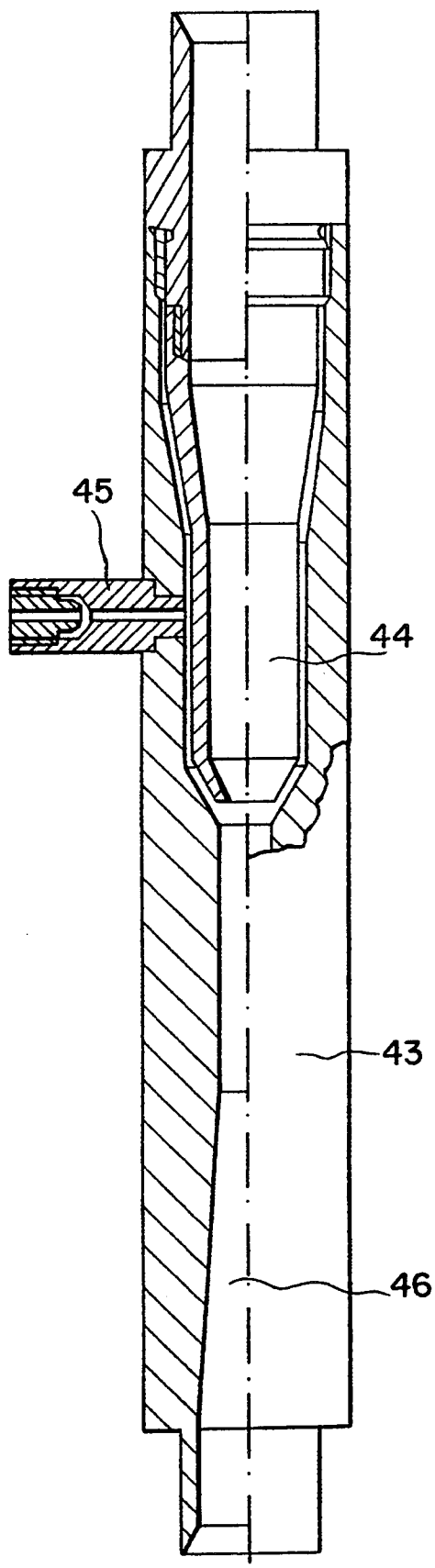
Figure 12:
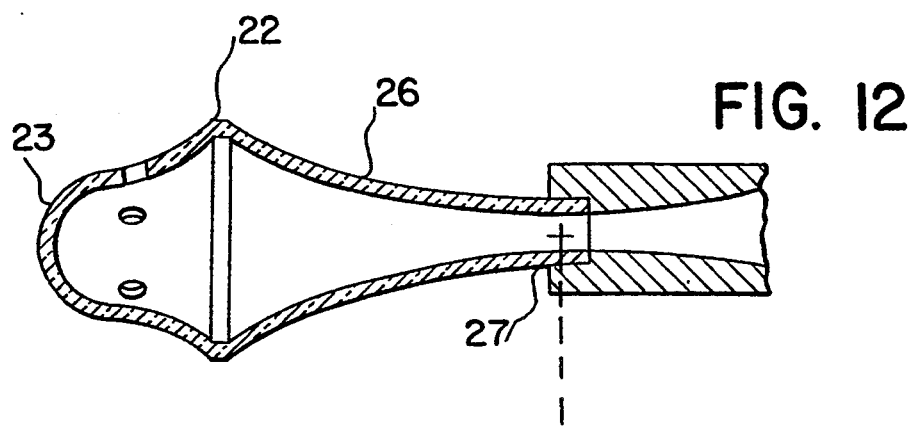
Figure 13:
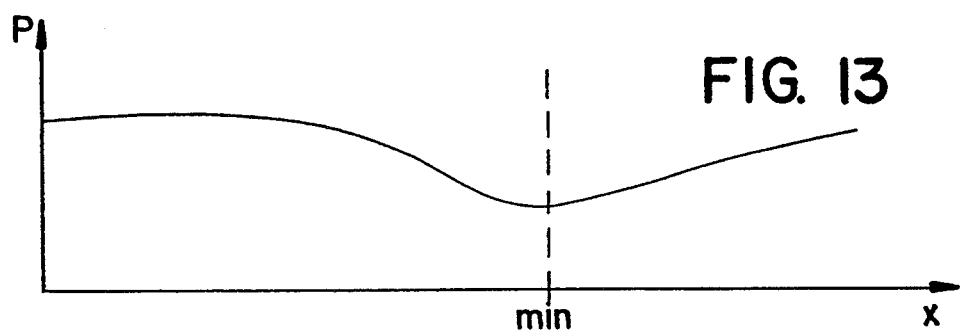
Figure 14:
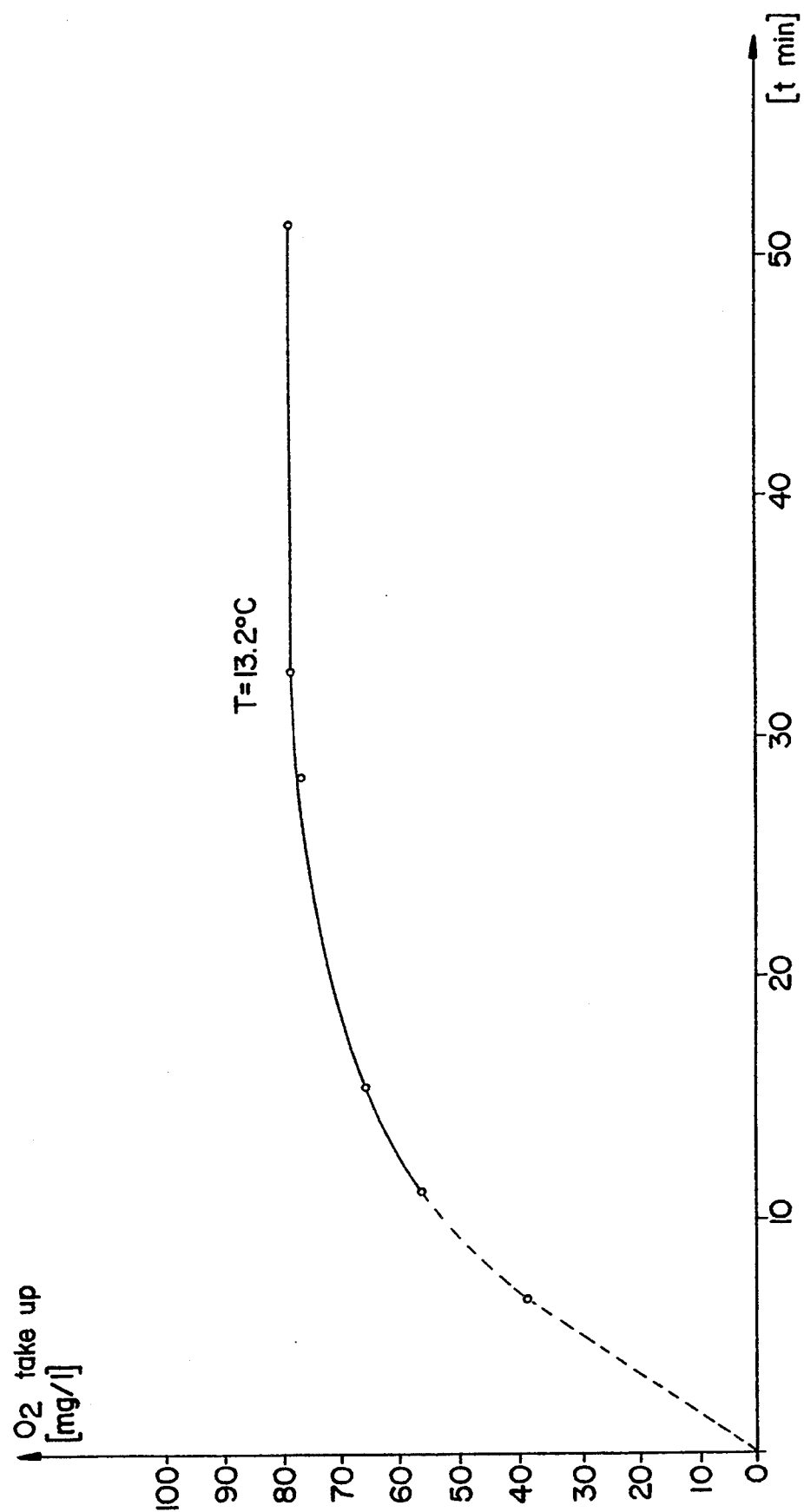
Figure 15:
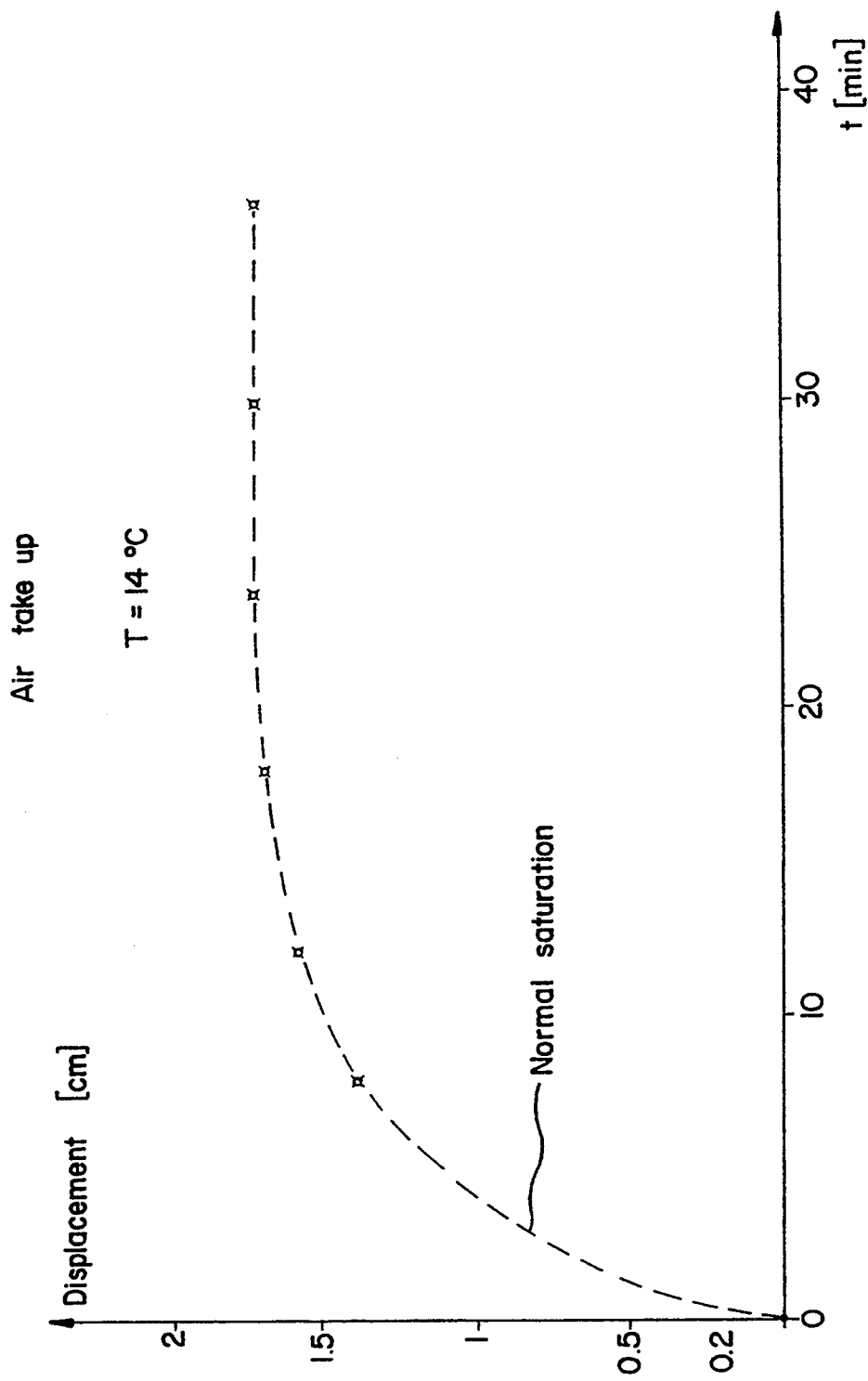
Figure 16:
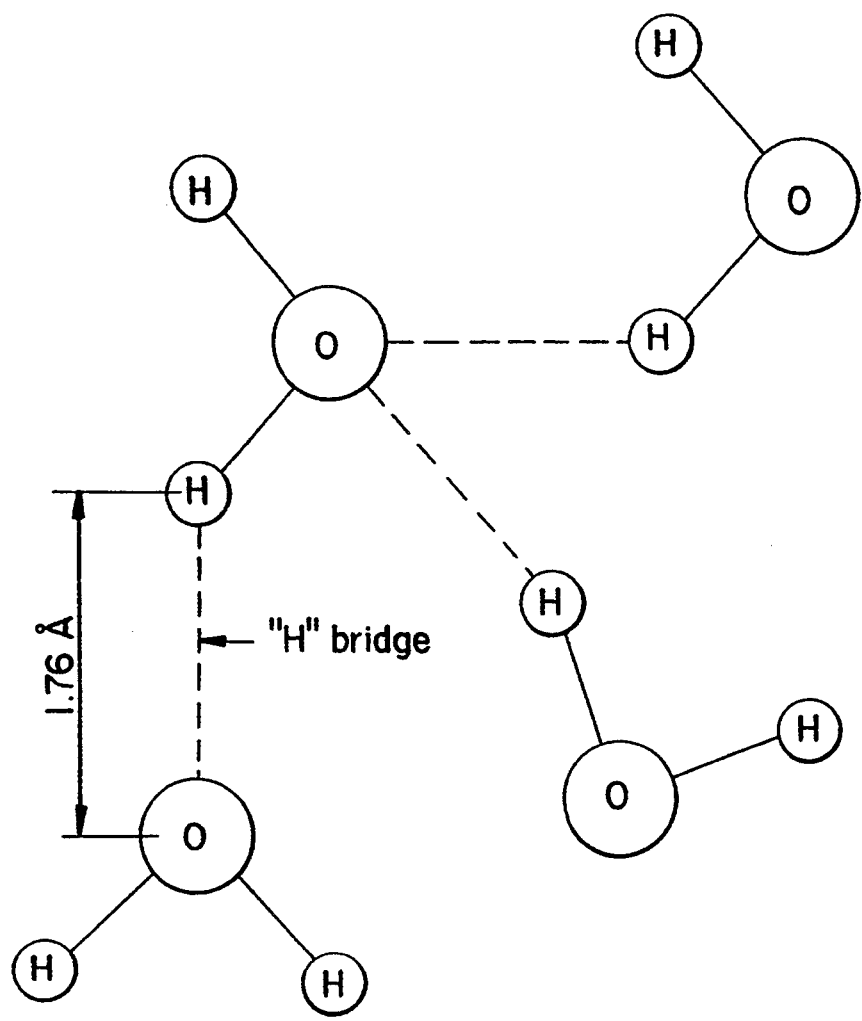
Figure 17:
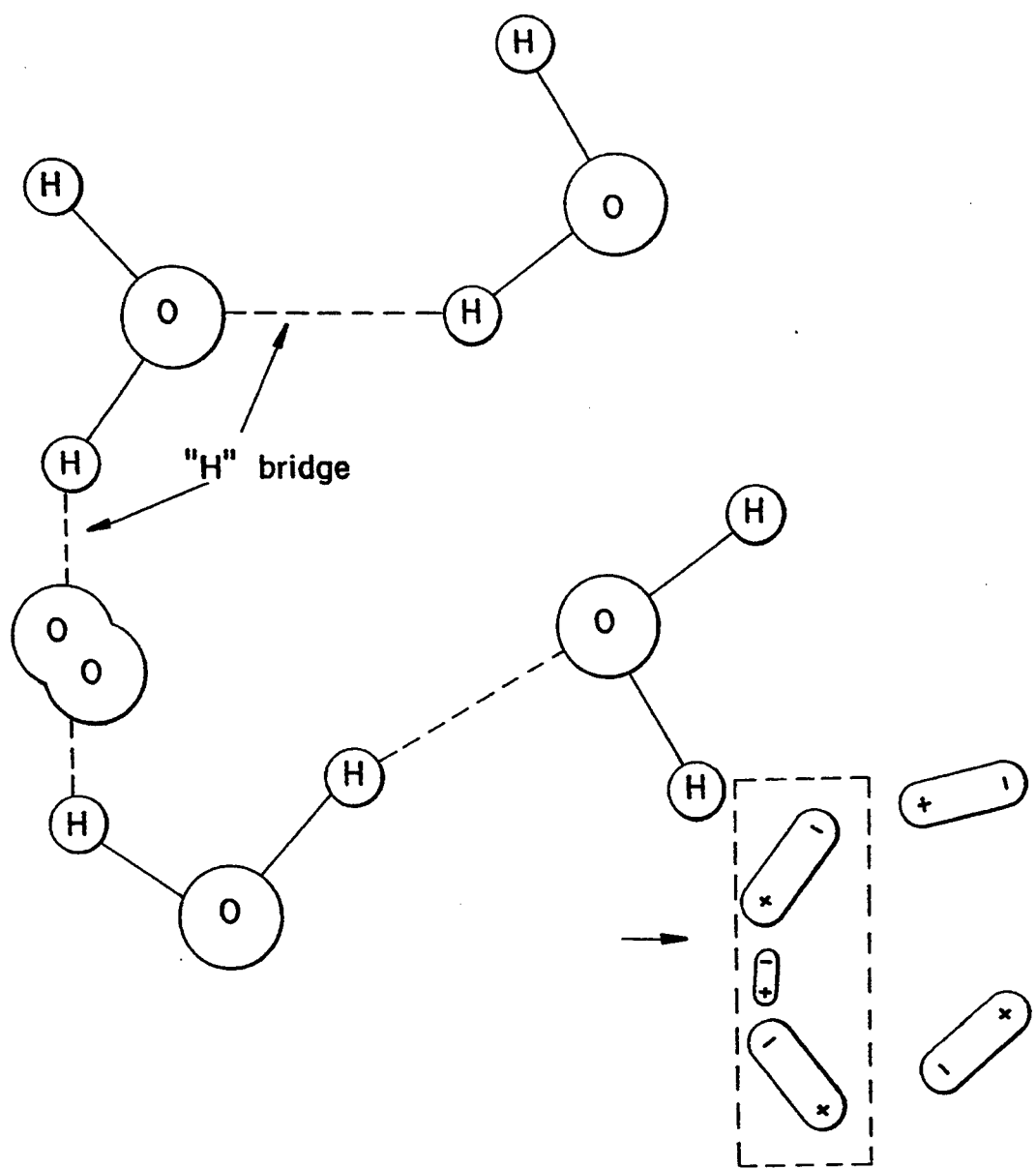
Figure 19:
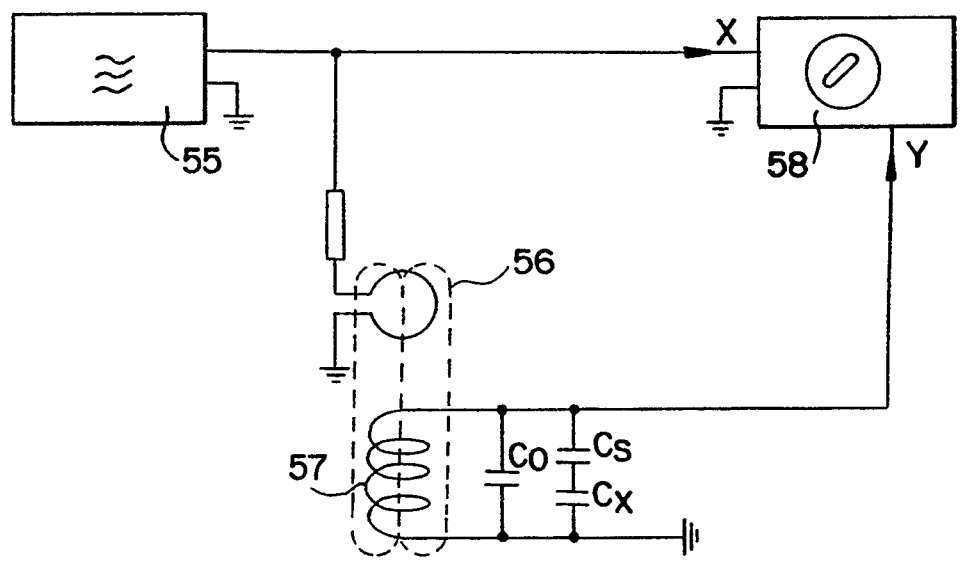
Figure 18:
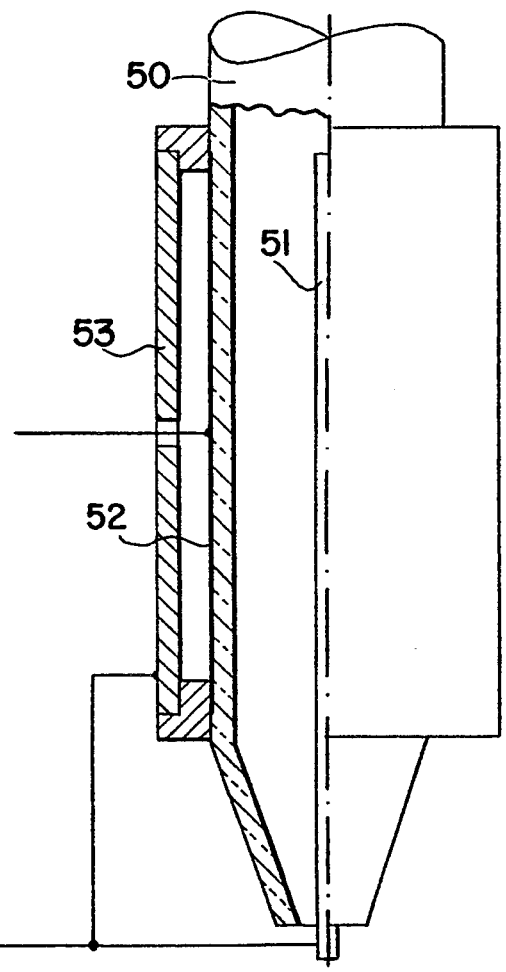
Figure 20:
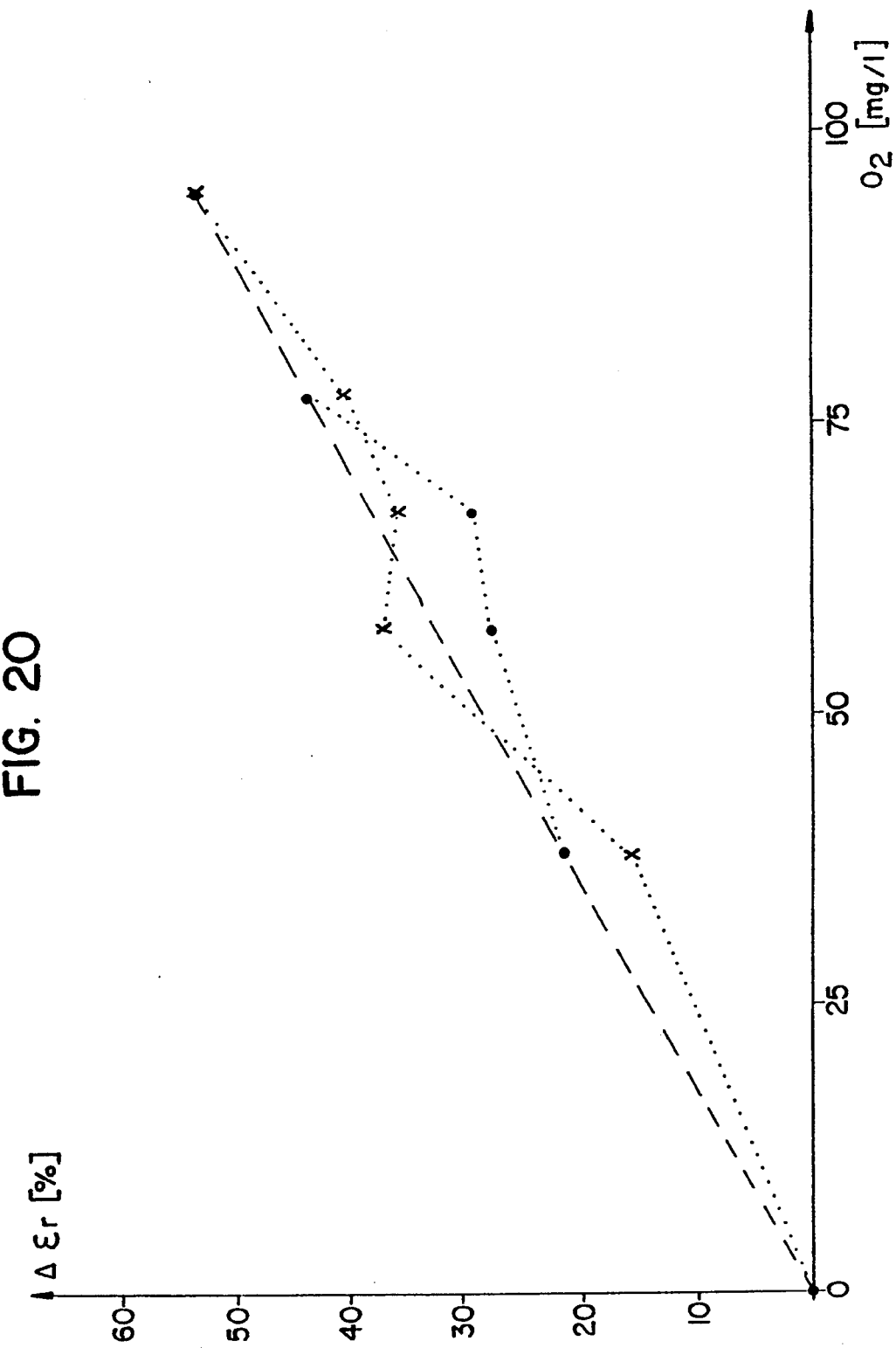

The invention will now be described in connection with preferable embodiments thereof, in which reference will be made to the accompanying drawings. In the drawing:

FIG. 1 shows the layout of a first embodiment of the apparatus according to the invention, FIG. 2 shows the elevation view of the reaction cheer of FIG. 1, FIG. 3 is a sectional top view of the reaction chamber in the plane of the holes, FIG. 4 illustrates a way how gas consumption is measured, FIGS. 5 to 7 show three sketches of the vortex in starting, medium and final phases of its formation, FIG. 8 shows an oxygen take up diagram as a function of time, FIG. 9 shows an improved embodiment similar to that shown in FIG. 1, FIG. 10 shows the layout of an alternative embodiment of the apparatus according to the invention, FIG. 11 shows the enlarged elevation view of the water jet pump of FIG. 10 partly in section, FIG. 12 shows the reaction chamber in section, FIG. 13 shows the pressure along the axis of the reaction chamber of FIG. 12, FIG. 14 shows the oxygen take up versus time curve for the embodiment of FIG. 10 in case of ion-exchanged water, FIG. 15 shows the air take up versus time curve for the embodiment of FIG. 10 in case of ion-exchanged water, FIG. 16 illustrates schematically the formation of hydrogen bridges bonding together water molecules as known in prior art, FIG. 17 is an illustration similar to that of FIG. 16 for the water according to the invention, FIG. 18 shows the enlarged elevational-sectional view of a sensor for measuring dielectric constant of water, FIG. 19 shows a circuit arrangement for measuring dielectric constant, and FIG. 20 shows the relative changes in the value of the dielectric constant as a function of oxygen content.

The general arrangement of the first embodiment of the apparatus used for carrying out the method according to the invention is shown in FIG. 1. Container 1 has a hollow interior which has a drop-like shape with a substantially spherical upper part 2, a medium part 3 which has a substantially hyperboloidal form that tapers in downward direction and an elongated slightly tapering lower part 4. The upper and medium parts 2, 3 are convex and the lower part 4 is concave. An inflexion plane is thus formed between the medium and lower parts 3 and 4. The interior of the container 1 is symmetrically arranged around an axis of rotation 5. In a preferable embodiment the container 1 is made of glass which enables the observation of the processes that take place therein. In the upper wall of the upper part 2 three ducts 6, 7 and 8 are provided of which ducts 6 and 7 are sealed.

The arrangement comprises a tank 9 filled with water. A cylindrical dish 10 is immersed with its open mouth in the water and a duct 11 is formed at the closed bottom of the dish 10. Flexible conduit 12 connects the duct 8 on the upper part of the container 1 with the duct 11 of the dish 10.

The container 1 has two further openings. A duct 13 is extending obliquely out of the upper portion of the medium part 2 substantially at a height in which the container has the largest diameter. The duct 13 closes respective acute angles with the equatorial and tangential planes of the container and its axis is directed slightly inwardly and upwardly towards the interior of the container. These angles are generally smaller than 30°. The second one of these further openings is the open lower end of the lower part 4 of the container 1.

A water recirculation path is provided between the lower end of the lower part 4 and the oblique duct 13 which comprises pump 14, reaction chamber 15 and three conduits 16, 17 and 18. The design of the reaction chamber 15 is shown in FIGS. 2 and 3.

The reaction chamber 15 comprises a cylindrical wall open at one end 19 and closed at the opposite end 20. A hollow element 21 is defined in this cylinder which has a circular rim 22 attached to the interior of the cylinder at the central portion thereof. A first part 23 of the element 21 has a form of a hollow rotational paraboloid which is located in the closed room between the rim 22 and the closed end 20 of the reaction chamber 15. In about one-third of the height of the paraboloid 23 a number of evenly distributed tangential holes 24 are provided through the wall of the element 21. In the exemplary embodiment this number is five. A duct 25 is extending out of the closed end 20 of the reaction chamber 15 which is slightly inclined relative to the axis of the reaction chamber. The element 21 comprises a second part 26 which communicates with the first part 23 at the plane of the rim 22 and this part has the form of a rotational hyperbola which is continued as a short cylindrical duct 27. In a preferable embodiment the reaction chamber 15 is made of glass.

It will now be explained how water enriched with a gas can be produced by means of the apparatus shown in FIGS. 1–3.

First, the sealed cork of the duct 7 is opened and 10 liters of normal tap water (e.g. such as available in Zurich, Switzerland) is filled in the container 1. The volume of the container 1 is such that the water level will be by about two inches above the duct 13. The duct 7 is closed and sealed again, the pump 14 is started and water is flown through the system so that any air present in the conduits 16, 17 and 18 as well as in the reaction chamber 15 will be released in the space above the water level. Now the pump is stopped and a cock attached to the duct 6 is opened, then oxygen is introduced through the water in the tank 9 in the inner space of the dish 10. The oxygen supply is sufficient to remove (push out) the air from the dish 10, from the conduit 11 and from the free space above the water level in the container 1. After a while the cock of the duct 6 is closed and pure oxygen will be filling the total gas volume in the container 1 and in the dish 10.

At this phase the water level in the dish 10 is equal to that in the tank 9.

In this arrangement the pump 14 is started. The pump has a flow output of 25 lit/min and the inner diameter of the conduits 16, 17 and 18 is equally about 16 mm. The direction of the flow is shown by the arrows in FIG. 1. When water is passed through the reaction chamber 15, it flows through the tangential holes 24 and a first vortex will be formed in the hollow paraboloid part 23 and of element 21. A component stream of the rotating water flows towards the closed end of the parabola and from here it will be reflected forward and unites with the other forward component, and owing to the exponentially tapering profile of the element 21 a rapidly rotating water stream will be established and flow in the conduit 18 towards the container 1. Arrow 28 of FIG. 1 symbolizes that this water is rotating in the conduit 18. The water flows tangentially into the container 1 through the oblique inlet duct 13.

In the container 1 the previously quiet water starts whirling and a second vortex is formed. The formation of the steady state of the vortex in the container 1 takes some time (about 1 or two minutes). We have taken a number of photos from the formation of the vortex and FIGS. 5 to 7 are the graphical representations of a few number of these pictures.

It can be seen in these pictures that after a diverse whirling a tornado-like vortex is formed, in which there is an almost cylindrical central hollow part which extends till the bottom of the lower part 4 of the container 1. The speed of the water particles in the vortex is very high. The number of revolutions at the uppermost and largest diameter of the vortex is about 50 r.p.m. and this speed is increased in downward direction approximately according to an exponential function. The speed can be calculated taking into account that the volume flowing through any given height is constant, thus the speed is proportional to the actual water cross-section around the vortex.

When the vortex has stabilized in the container 1, the pump 14 keeps running. After a while the water level starts increasing in the dish 10 relative to the level in the tank 9. This indicates that a portion of the oxygen present in the volume above the water has been taken up by the circulating water.

FIG. 4 shows schematically how the quantity of oxygen taken up by the circulating water has been calculated. The original water level in the dish 10 is indicated by the reference numeral 29. The level increase is expressed by H. The cross-sectional area of the dish 10 is designated by A. The oxygen take up can be expressed as $V = A \times H$.

It is known that the density of oxygen is $d = 1.43$ mg/cm$^3$ at 0° C. If we wish to express the consumed oxygen in mg units, then the oxygen mass in milligrams will be $m = d \times A \times H$. The $A \times H$ product should be in cubic centimeter units.

This oxygen is taken up by the water volume. If the relative quantity of the oxygen in the circulating water has to be expressed, then $C_o = d \times A \times H / V_w$ should be calculated. This formula expresses the excess oxygen taken up by the water during the process in mg/l units if the volume of the water $V_w$ is expressed in liters.

It can well be supposed that the tap water that was filled in the container 1 was almost saturated with dissolved oxygen, since normal tap water after some time of free running gets practically saturated. In room temperature this corresponds substantially to a concentration of 9 mg/l.

In the exemplary embodiment the diameter of the dish is 10 cm, and the volume of the water $V_w = 10$ liter. Substituting these data in the expression for the oxygen concentration, it is obtained that $C_o = 11.225$ H. If H is measured in cm units, $C_o$ will be in mg/l units in case of T=0° C., and $C_o = 10.46$ H at T=20° C.

The full oxygen concentration will be obtained if the starting concentration is added to the calculated value.

Table 1 below summarizes the measured and calculated results of a test series carried out between May 13 and Jun. 3, 1987.

TABLE 1

| Day/month/hour | time elapsed (hours) | Temp. (°C.) | H (cm) | C$_o$ increase (mg/l) | C$_o$ total (mg/l) |
|---|---|---|---|---|---|
| 13.5 12.00 | — | 18 | — | — | 9 |
| 14.5 12.00 | 24 | 21 | 1.8 | 18.82 | 27.82 |
| 15.5 17.00 | 29 | 22 | 3.0 | 12.57 | 40.39 |
| 17.5 11.00 | 42 | 19 | 5.0 | 11.92 | 52.31 |
| 18.5 08.00 | 21 | 19 | 5.8 | 8.38 | 60.69 |
| 19.5 08.00 | 24 | 21 | 6.4 | 6.28 | 66.97 |
| 20.5 08.00 | 24 | 21 | 7.2 | 8.36 | 75.33 |
| 21.5 08.00 | 24 | 20 | 8.0 | 8.36 | 83.69 |
| 22.5 08.00 | 24 | 19 | 8.7 | 7.36 | 91.05 |

TABLE 1-continued

| Day/month/hour | time elapsed (hours) | Temp. (°C.) | H (cm) | C$_o$ increase (mg/l) | C$_o$ total (mg/l) |
|---|---|---|---|---|---|
| 23.5 13.00 | 29 | 24 | 9.7 | 10.48 | 101.53 |
| 25.5 13.00 | 48 | 22 | 12.0 | 24.11 | 125.64 |
| 30.5 13.00 | 120 | 19 | 19.0 | 73.37 | 199.01 |
| 1.6 16.45 | 51.75 | 21 | 20.3 | 13.6 | 212.61 |
| 3.6 07.30 | 38.75 | 21 | 21.3 | 10.48 | 223.09 |

The value of 9 mg/l in the first row of the total concentration column corresponds to the original dissolved oxygen concentration of the water.

FIG. 8 shows the data given in Table 1 in diagrammatic form. The experiment with water was finished on Jun. 3, 1987. At this time the pump was switched off and the closed system was left alone. In further five days the height difference remained unchanged which was an indication that the gas taken up by the circulating water remained in bound state in the water. This result demonstrates that there was no gas leakage in the apparatus either.

The container 1 was opened after the fifth day and the oxygenized water was filled in 0.1 and 0.2 liter glass bottles under normal pressure.

A conventional dissolved oxygen test was carried out on a sample taken from that oxygenized water by a Yellow Springs Instruments Co. Inc Model 54 Oxygen Meter at a temperature of 20.5° C., and the instrument showed a dissolved oxygen concentration of 8.5 mg/L only. In a later part of the specification it will be explained why conventional dissolved oxygen test methods are believed to be inappropriate to detect oxygen taken up according to the present invention.

Reference will be made now to FIG. 9 which shows an apparatus similar to that shown in FIG. 1. The container 1, the pump 14, the water tank 10 as well as the dish 10 are those used in the first embodiment. In the path between the outflow duct of the pump 14 and the inflow duct of the container a temperature regulating device 30, preferably a heat exchanger is provided by which the temperature of the circulating water can be adjusted to a constant value. Instead of the single reaction chamber 15 shown in FIG. 1 three similar reaction chambers 15a, b and c are used which are connected in parallel with each other. As it will be apparent from later parts of the specification the specific bonding of the oxygen gas to the water takes place in the reaction chamber. When the number of the reaction chambers is increased, more oxygen can be bound in a given period of time. The vortex in the container 1 is believed to has the task of supplying oxygen in the water. According to experiments made with different pump speeds the process is at optimum when the lower end of the vortex in the container (shown separately in FIG. 7) is somewhere at the outflow duct of the container 1 or extends slightly in the conduit 16. In a given constructional design this condition is fulfilled at a given pump speed. The optimum conditions for the reaction chamber 15, as will be explained later, depend on the pressure distribution and on the flow rate, and these conditions should be matched with the flow rate associated with the optimum vortex. By appropriate dimensioning of the form and cross section of the reaction chamber as well as of the number of reaction chambers connected in parallel it can be achieved that the flow rate providing optimum vortex will coincide with optimum reaction in the reaction chambers.

It should be noted that turbulence in the recirculating flow of water can disturb the process therefore sudden changes of cross sections should be avoided. The pump 14 should be a type which does not generate turbulence either. Conventional rotary or peristaltic pumps satisfy this criterion.

In the gas path between the dish 10 filled with oxygen and the container 1 a condenser 31 is inserted. This can be a tank in which a portion of the gas conduit is lead through and in the tank a cooling medium e.g. ice is provided that cools down the wall of the conduit so that vapor supplied by the inevitable evaporation of water contacting the gas will be condensed. The use of condenser 31 stabilizes the partial oxygen pressure in the closed space above the water surface which would otherwise decrease due to ever increasing amount of vapor. This is true, since the sum of the partial pressures of oxygen and vapor is always equal to the atmospheric one.

A substantially more effective embodiment of the apparatus according to the invention is shown in FIG. 10.

In this embodiment a cylindrical container 34 is used which has a sealed cover and a five tubes extend therethrough. The container is filled with water, in the exemplary embodiment four liters fill the container as illustrated in the drawing. Of the five tubes crossing the cover the second one from the left is immersed deeply in the water and the outer end thereof is connected via a conduit to inlet of recirculating pump 14 designed just as in the previous embodiments. The outflow conduit of the pump 14 leads to water inlet of a water jet pump 35. The internal structure of the water jet pump 35 is illustrated in FIG. 11. The water jet pump 35 has an outlet connected to inlet of a reaction chamber 15 designed as shown in FIGS. 2 and 3 in the previous embodiments. Diffusor 36 is connected to the outflow duct of the reaction chamber 15 to increase the cross-section of flow to the uniform cross-section of conduits used in the recirculating path. This path has been illustrated in FIG. 10 with heavy line. A conduit connects the diffusor 36 to the fourth tube 41 which extends till the upper water level only. When the pump 14 is operated a water recirculation takes place.

The free space above the water level in the container 34 communicates through the fifth tube and four port distributor 40 with the inner space of dish-10 immersed in tank 9. This fully corresponds to the previous embodiments and the use of the dish 10 and of the tank 9 is the simple indication of oxygen take up by means of reading the displacement of the water level.

An additional closed gas recirculating path has been provided which comprises the third tube 38 inserted in the container 34 to extend till the gas space above water level, a conduit connects this tube to gas pump 39 via a meandering portion in condenser 31 and the other port of the gas pump 39 is connected to a port of the distributor 40 which is connected again to the inner gas space of the container. When the gas pump 39 is running, a gas recirculation takes place, and vapor comprised in the gas will be effectively condensed. The water jet pump 35 has a port for sucking in gas which is connected to the fourth port of the distributor 40.

The first tube which extends in the water through the cover is a temperature sensor connected to thermometer 37 by means of which the temperature of water can be controlled. The temperature regulation of the apparatus shown in FIG. 10 is solved in such a way that a conventional household refrigerator 32 is used and the container 34, the tank 9 with the dish 10 as well as the water jet pump 35 and the reaction chamber 15 are arranged in the inner space thereof. The condenser 31 is a tank arranged in deep freezer 33 of the refrigerator 32 filled with a cooling fluid which can effectively cool down the meandering gas conduit immersed therein to condense vapor.

The use of the refrigerator serves, of course, experimental purposes, the temperature stabilization and condensation of water can be solved by more effective means as well. An advantage of using the refrigerator 32 lies in that the free inner space thereof can be filled with oxygen gas. The oxygen gas present in this space cannot communicate with the closed inner space of the assembly in which fluid is recirculated, however, if oxygen gas is present around the water seal provided by the tank 9, then there will be no diffusion through the water at all, and the quality of the sealings of the container 34 and of the conduits will not be too critical any more, since oxygen gas fills both the inner and outer spaces. The oxygen supply is provided through water seal 42 from a gas source not shown in the drawing.

The water jet pump 35 has the main task of supplying oxygen into the water in the form of fine vapor in a quantity which can be bound to the water in the reaction chamber 15. The water jet pump 35 has a substantially cylindrical housing 43 shown in FIG. 11 defining a hollow inner space. Water nozzle 44 is inserted in the hollow inner space of the housing 43 and the upper end thereof communicates with inlet duct to which the conduit coming from the pump 14 can be fitted. A cylindrical space is defined around the mantle surface of the nozzle and a radial gas inlet duct 45 is inserted in the wall of the housing 43 so that the hollow interior space of the duct 45 communicates with the space around the nozzle 44. A removable bolt with a central bore can be inserted in the hollow space of the duct 45 and the gas supply can be adjusted by using a bolt with appropriate bore. The housing has a cylindrical hollow section in front of the mouth of the nozzle which communicates with diffusor 46 that provides a transition between the smaller cross-section of this cylindrical section and the larger one of outflow duct.

Optimum recirculation is obtained if in the whole recirculation path shown in FIG. 10 with heavy line has a uniform cross-section. In the examplary embodiment the diameter of the conduits in this path is 16 mm.

In operation water streams through the mouth of the nozzle 44 with a higher speed owing to its smaller cross-section and this is accompanied with a decrease in pressure. This vacuum sucks gas in through the gas inlet duct 45 and in the cylindrical section past the mouth of the nozzle 44 oxygen is vaporized and swallowed by the water stream.

In operation the apparatus shown in FIG. 10 should be adjusted so that the following considerations are taken into account.

The water recirculating system should be designed in such a way that cavitation cannot take place. The flow should therefore be continuous and free of turbulences. This condition applies to the pump as well. The flow of the pump 14 can be changed by adjusting the speed of rotation. In the examplary embodiment a rotary pump was used which had a flow of 3000 liters/hour if the speed was 2500 rev/min.

The form and size of the reaction chamber 15 should define the flow rate at which oxygen takeup occurs.

This flow can be adjusted by changing the speed of the motor.

The adjustment of the flow rate should start with testing the properties of the reaction chamber 15 alone. This can be done by connecting the input and output ducts of the reaction cheer 15 through the pump 14 in a closed loop and water is recirculated therethrough. The glass housing of the reaction cheer 15 is transilluminated by an ultra violet light source which helps visual detection of bubble formation. If the flow rate of the pump is increased from a minimum, there will be a flow rate at which small bubbles emerge and can be seen around an axial section of the reaction cheer substanbtially where the cross-section is at minimum. FIG. 12 shows the sectional view of the second part of the reaction chamber 15 with the exponentially tapering portion 26 that continues in a cylindrical form and to which a diffusor (element 36 in FIG. 10) is connected. FIG. 13 shows the changes of the pressure along the axis of the reaction chamber. This pressure curve represents at the same time the minimum pressure in the concerned half chamber, since the pressure increases with the radial distance from the axis due to the braking effect of wall frictions. The flow rate is at maximum at the medium zone, hence the pressure is at its minimum there.

The pressure along the axis as shown in FIG. 13 decreases, reaches a minimum, this minimum is maintained in the short cylindrical section then it increases again due to increasing cross-section of the diffusor. In case of water in a given temperature there exists a pressure at which the internal vapor tension is equal therewith and when such pressure is reached boiling starts. When bubbles are detected along the axis at the minimum pressure zone indicated in FIG. 12 by a short light line it means that the pressure has reached the critical value at which boiling starts. In the pressure curve of FIG. 13 we can observe that further away along the direction of flow the pressure increases again, and in this pressure value the boiling conditions are not met any more, therefore the flowing bubbles of vapor will be condensed. The viewer can see therefore a short thread-like section of gas phase only. This flow rate corresponds to the start of cavitation in the reaction chamber 15 which will be referred to as critical rate.

In the process according to the invention a flow rate slightly smaller than the critical rate is adjusted. The apparatus shown in FIG. 10 should then be assembled and the free spaces should be filled with pure oxygen. In operation the water jet pump 35 supplies oxygen in the water which will comprise therefore a small amount of oxygen.

In the reaction chamber 15 the oxygen gas streams i.e. collects at the pressure minimum which is the same axial section where previously bubbles emerged at the critical rate. The concentration of the gas along the axis is assisted be the rotational flow around the axis due to tangential inlet in the reaction space. The oxygen gas will take the form of small bubbles and the size of which depends on the surface tension of water, on the actual pressure and on the flow rate. These small bubbles get saturated also with vapor and as they flow in forward direction the pressure increases and the vapor gets condensed in the presence of oxygen gas. It is believed that oxygen gets bound to water in this section. The energy relations in this section defined immediately past the zone of minimum pressure closely correlate with the surface tension of water. From this phenomena the viewer can see a tiny short line of fine bubbles along the critical axial section indicated in FIG. 12.

The gas supply of the water jet pump 35 should be adjusted so that this tiny line be continuously present and possibly no other bubbles can be seen in the whole system past the reaction cheer. The presence of certain bubbles in the first (inflow space) of the reaction chamber can be tolerated. If the gas supply is higher, then the excess gas will bubble out of the liquid.

It should be mentioned that the operation of the first embodiment of the invention is similar, there the large surface of the vortex catches a small amount of gas and supplies it into the water and this gas will take part in the reaction in the reaction chamber 15. With such embodiment the adjustment of the flow rate is rather critical, since the flow rate which is optimum for the reaction should generate a proper vortex which can ensure the required oxygen supply.

A typical oxygen take up test carried out by the apparatus as shown in FIG. 10 will now be described as an example.

The container 34 was filled with 4 liters of ion-exchanged water (from which both cations and anions were removed), air was thoroughly removed from the space above the water level by means of sufficient oxygen supply, whereafter oxygen filled this space. The inner space of the refrigerator 32 was also filled with oxygen. The ambient temperature was 28° C. and the temperature of water was adjusted to 13.2° C. A sample was taken from the starting water. The pump 14 was started and in a short time the water level started increasing in the dish 10. In order to eliminate any dynamic effect on the reading of the height difference, the pump 14 was switched off and the reading of the height was measured when the level has already stabilized. To improve accuracy after each measurement of the pressure difference fresh oxygen was introduced in the system by means of a valve in the distributor 40, whereby the water level in the dish 10 and in the tank 9 became equal. The height difference was calculated to oxygen take up in mg/l units by means of simple calculation and the oxygen take up curve is shown in FIG. 14. The dashed portion of the take up curve corresponds to normal saturation. The time is the active time, i.e. the timer was stopped when the level measurements were made. In each measurement respective samples were taken.

It can well be seen from FIG. 14 that oxygen take up did not increase above 80 mg/l at this temperature and in case of this water. The take up time is substantially shorter than in case of the embodiment using vortex for oxygen supply. When the saturation was reached, the pump was stopped and the system was kept for 24 hours. The water level in dish 10 did not change which means that the supplied gas remained in the water.

We have carried out several tests and they all correspond to that shown in FIG. 14. The 80 mg/l oxygen is contained in the water in bound state and this concentration remained when the water surface was exposed to air. This concentration is about 9 to 10 times as high as normal saturation of water with oxygen.

It should be noted that the speed of oxygen take up increases with decreasing temperature and the process substantially slows dow when the temperature is above about 23° C.

In addition to the examination of oxygen take up a test for air take up was carried out. In that case the space in the container 34 was filled with atmospheric air and air was present in the refrigerator 32 as well. FIG. 15 shows a similar take up curve, in which the vertical axis was expressed in overall displacement. The displacement that corresponds to normal saturation of water with air was at a displacement of 0.8 cm and the take up reached the maximum value of 1.9 cm in 30 minutes.

It should be noted that the take up with tap water was more intensive and the saturation occurred at higher displacements if tap water was used. Owing to the indefinite composition of tap water the use of ion-exchanged water can be justified.

Now a hypothesis for the bonding of oxygen by water will be given, and the truth of which will be demonstrated by the results of further measurements made on the samples taken from various phases of the process.

In the description of the prior art portion of the specification reference was made to the polymeric structure of water and to the fact that hydrogen bridges connect molecules in such structures. FIG. 16 is a sketch illustrating such hydrogen bridges between four water molecules.

A hydrogen bridge cannot select between the adjacent oxygen atoms with which it will be connected, since the $O_2$ gas (if present) may have electrons in sigma and pi state in the same way as the oxygen bound in monomer water has. It is possible therefore that such hydrogen bridges are created in the oxygenized water, in which the $O_2$ molecules are bound to respective hydrogen atoms of two different monomer water molecules. Such a structure is shown in FIG. 17 in which an oxygen molecule that takes an elongated form is bound by two hydrogen bridges to two water molecules.

If such a bonding is possible and it is present in the water as produced according to the invention, then the originating $O_2$ molecules, which had induced dipole moments only, when being bound between two hydrogen bridges will now create additional dipole moments in the water polymer. The existence of this additional dipole moment has to change (increase) the dielectric constant of this water.

To verify this hypothesis a dielectric constant measurement was carried out on the samples. FIG. 18 and 19 illustrate the measuring arrangement used for determining the dielectric constant. A pipette 50 having a hollow interior was used to contain water samples. Along the axis of the hollow interior a graphite rod 51 was provided which formed an electrode. The cylindrical outer surface of the glass wall of the pipette was covered by a conductive layer 52 and spaced by a distance around this layer a shielding cylinder 53 was arranged. A measuring capacitance was formed between the earthed rod 51 and the cylinder 52 which was connected in parallel with the capacitance $C_o$ between the earthed shield 53 and the cylinder 52. The capacitance of the water sample $C_x$ was connected in series with a constant capacitance $C_s$ formed by the glass material between the water and the cylinder. A substitute circuit arrangement with these three capacitances can be seen in FIG. 19. The resulting capacitance was connected in parallel with inductance 57 to form a resonance circuit and a coil 56 was inductively coupled to the inductance with a loose coupling. A signal generator 55 delivering very accurate and stable sine signal of variable frequency was used to supplied horizontal deflection of an oscilloscope 58 as well as to excite the resonance circuit. The vertical deflection of the oscilloscope 58 was driven from the resonance circuit.

The unknown dielectric constant was included in the capacitance $C_x$ and the relative changes of the capacitance $C_x$ could be expressed as the function of the resonance frequencies. In the measurement the frequency of the generator 55 was set to a value at which a standing Lissajous curve of a predetermined phase was seen on the oscilloscope, first when the ion-exchanged starting water sample was introduced in the pipette 50. Then the sample of oxygenized water was introduced in the pipette and the same resonance and phase condition was set again. The two frequency values served as a basis for calculating the relative dielectric constant of the sample. Although the available test equipments were not at optimum, the error of the measurement of the dielectric constant was at any case below 10% and at an average i was below 5%.

FIG. 20 shows two independent series of tests made on samples taken from the same water. There was a two day's delay between the two measurements which show the relative change of the dielectric constant as a function of oxygen content in the water. The diagram shows that a substantial increase in the dielectric constant can be experienced as a function of oxygen present in the water. On the first hand this result supports the above hypothesis, and on the other hand surprisingly high (otherwise not attainable) dielectric constants are obtained. The relative change of the dielectric constant appears to vary linearly with the oxygen content. The two tests gave similar results, therefore in two days there was no structural change in the sample that proves stability.

In case of the air take up measurements intermediate samples were not taken, the dielectric constant of the water obtained by the end of the process was by 83% higher compared to the starting water. This is a more significant increase than in case of pure oxygen, and makes it likely that nitrogen present dominantly in air has also been bound to water molecules.

In the following further test results supporting the above hypothesis will be demonstrated.

A water sample oxygenized by the apparatus shown in FIG. 1 was examined by electron spin resonance technique. It is known that the $O_2$ molecule possesses an uncompensated electron spin, thus it forms one of the most paramagnetic gases (or liquids below its critcical temperature). The oxygen compounds, however, including water are diamagnetic and from this rule there are only a few number of exceptions.

The state of the art electron spin resonance measurements are appropriate for the detection of paramagnetic resonance by absorption if the minimum number of uncompensated electrons (which have no pairs) in the samples amount to $10^{10}$. With such sensitivity the dissolved oxygen present in water at saturation level at atmospheric pressure and at room temperature which is about 8–9 mg/l cannot be detected, since with such amount of dissolved oxygen the number of uncompensated electrons will be slightly less than the threshold sensitivity. Taking into account this sensitivity and supposing that oxygen is present in the oxygenized water made according to the invention water in free (dissolved or unbound state) in the concentration far above normal saturation, then this concentration would produce such number of uncompensated electrons which could well be detected i.e. be distinctively visible in the diagram of ESR measurements.

The measurement was carried out with the instrument ESR 200 (East German type). A sample was used which was treated by the apparatus as shown in FIG. 1 using tap water available in Zurich and the oxygen take up curve of the water from which the sample was taken followed the diagram of FIG. 8. The maximum of the absorption of the paramagnetic resonance peak of dissolved oxygen was expected to fall on the section between the 4th and 5th vertical marker line at the horizontal axis. The actual curve, however, showed even at maximum sensitivity no distinctive identification but a background noise only.

This measurement proves that the sample from the oxygenized water did not comprise the oxygen in a physically dissolved state otherwise the paramagnetic resonance were detectable. This is an indirect proof that the excess oxygen takes a bound state in which the spins are compensated. In other words the ESR measurements exclude that the excess oxygen can be present in pure dissolved state (i.e. in gas phase). With regard to the fact that chemical bonding cannot be responsible for the presence of excess oxygen, since no chemical was present in the water, it should be assumed that this oxygen is kept by weak interaction forces (hydrogen bridges), thus a further support for the above hypothesis has been found.

If this hypothesis is true, then at any given temperature the oxygenized water must have a higher grade of structure than normal water has i.e. the parameters of oxygenized water should correspond to those of normal water at lower temperatures in which water gets more structured.

From the oxygenized water used for the ESR measurements further samples were taken and a number of physical parameters thereof were measured. Before reporting on the results of such measurements, the expected changes are worth being analyzed in advance. It is assumed again that oxygen is present in the water in a physically dissolved state.

The molcecular weight of water is approximatively 18, since each molecule comprises an oxygen atom with an atomic weight of 16 and two hydrogen atoms each having an atomic weight of 1. From this it follows that the amount of oxygen mass in water is 16/18. If we assume that 1 liter water has a mass of 1 kg, then the oxygen mass is 888.8 gram.

If we suppose that the oxygen amount is 240 mg/l, then the relative increase in oxygen mass can be expressed as $0.24/888.8 = 2.7 \times 10^{-4}$ which is as small as about three tenthousandth. From this proportion the expected changes in the density, surface tension, viscosity, gas tension and optical refraction compared to those of normal water measured at equal temperature will be about $2.7 \times 10^{-4}$ if a linear connection is supposed to exist between the increase of the oxygen content and these parameters. This assumption may not be correct but it has been taken as a rough estimate value to assist making comparisons. The term "normal water" refers to double distilled water used during the measurements as control.

The results of the measurements are summarized in Tables 2 and 3.

TABLE 2

| Parameter measured | number control water | oxygenized water relative to ctrl. | probability |
|---|---|---|---|
| Density | 6 ± .0001 | 1.0002 ± .0002 | 8% |
| Surface tension | 20 ± .01 | 1.03 ± .01 | 1% |
| Viscosity | 20 ± .003 | 1.010 ± .003 | 1% |
| Gas tension | 3 ± .6 | 1.4 ± .2 | 20% |
| Optical refraction | 20 ± .0005 | 1.0012 ± .0006 | 1% |

| Parameter measured | Temperature | oxygenized water | dimension |
|---|---|---|---|
| Density | 21.2 | .99795 | g/ml |
| Surface tension | 22.0 | 74.43 | din/cm |
| Viscosity | 21.5 | .9788 | centipoise |
| Gas tension | 22.6 | 20.65 | Hgmm |
| Optical refraction | 21.1 | 1.3331 | at 589 m/u |

The first column refers to the number of repetitions of the associated measurement. The column labelled as "control water" gives the accuracy of the measurement made on the control water. The average of the measurement was given a value 1 and the column "oxygenized water" comprises the relative value of the average of the n measurements compared to the control and the associated accuracy. The last column shows the probability p obtained by the "t" test. If p is less than 5%, then the result can be regarded as acceptable i.e. sufficiently significant. If p is less than 2.5%, then the result is very significant i.e. the result can be accepted as a sure one. The result of the "t" test i.e. of the value of the probability p is highly dependent on the number n of the repetitions. If only few number of measurements were carried out, the value of p can be as high as 20% or higher, and this need not always mean that the reliability of the result is poor.

The second part of the table gives the average values of the measurements of the associated parameter made on oxygenized water expressed in the dimension given in the last column. The temperature values were also given.

Considering the results shown in Table 2 it can be stated that the surface tension, the viscosity, the optical refraction of the oxygenized water are definitely, while its density and gas tension are probably higher than corresponding values of the control water.

In Table 3 the changes in the measured values will be compared with the expected change of $2.7 \times 10^{-4}$.

TABLE 3

| | |
|---|---|
| Surf. tension: | 111-times higher than expected; very significant |
| Viscosity: | 37-times higher than expected; very significant |
| Gas tension: | 1481-times higher than expected; not significant |
| Opt. refract.: | 4.44-times higher than expected; very significant |

The change in density was somewhat less than expected, the measurement was not significant and there is a problem that the change of density cannot be predicted, since it largely depends on the hydratation of the anorganic ions.

From Table 3 it follows that the changes in the measured physical parameters were much higher compared to the expected value which would be justified by considering the proportion of 240 mg/l oxygen. The sense of the changes correspond to values which can be measured in the control water when its temperature is much smaller. The physical measurements have proved again the above described hypothesis, since in a given temperature the sample behaves as if it were more structured (or cooler) than normal water.

The dielectric constant of the sample was determined by a pipette which was less sensitive than that shown in FIG. 18, and a relative increase of about 25% was determined. It should be noted that the sample had some conductivity due to the presence of various anorganic ions in the original tap water. The conductivity exerts an influence on the measurement of dielectric constant in the arrangement shown in FIG. 19 therefore the 25% value is rather an indication of the increasing tendency of the dielectric constant than an accurate value.

The tests reported hereinabove related to oxygen or air. The method according to the invention is also useful when carbon dioxide is added to water in superequilibrum quantity. A test for introducing carbon dioxide to ion-exchanged water was made by means of the apparatus shown in FIG. 9 using three parallel reaction chambers 15a, 15b and 15c. Owing to certain limitations the condenser 31 and the cooler 30 were not used.

The speed of the motor had to be decreased substantially, about to a rate of 750 l/hours from the original value of 3000 l/hours since with speed used for oxygen or air take up intensive bubble and foam formation took place. Table 4 summarizes the carbon dioxide take up.

TABLE 4

| Active time | Sum active time | Passive time | Displ. cm | Sum displ. cm | Concentration c.c./l |
|---|---|---|---|---|---|
| 18 s. | .3 min | | 18 | 18 | |
| 23 s. | .68 min | | 17.5 | 35.5 | 544.3 |
| 38 s. | 1.316 min | | 17.0 | 52.5 | 804.95 |
| 3 min 14 s. | 4.549 min | | 15.0 | 67.5 | 1034.94 |
| 10 min | 14.549 min | | 1.0 | 68.5 | 1050.27 |
| | | 15 h. | 10.0 | 78.5 | 1203.6 |
| | | 6 h. | 2.7 | 81.2 | 1244.99 |
| 9 min | 23.549 min | | 3.7 | 84.9 | 1301.72 |
| 7 min | 30.549 min | | .8 | 85.7 | 1313.99 |
| 7 min | 37.549 min | | .5 | 86.2 | 1321.66 |
| | | 14 h. | 10.2 | 96.4 | 1478.05 |
| 10 min | 47.549 min | | 5 | 101.4 | 1554.71 |

In this table the active time designates the time when the pump was running and the process took place. The reading of the displacement values occurred when the pump was switched off. During the passive periods carbon dioxide filled the space above the water level.

The test was carried out when the temperature of water changed between 18.3° and 18.8° C. At this temperature normal saturation of water with carbon dioxide is 930 c.c./liter.

During the take up the water volume increased from the original 8 liter value to about 8.5 liters. The increase of the displacement during the passive periods can be attributed to the fact that the water seal provided in the tank 9 is less effective for carbon dioxide and a diffusion through the water takes place.

If we deduce the partial take up values during the passive periods, i.e. a combined value of 351.11 c.c./l, then the resulting carbon dioxide take up is 1203.6 cm$^3$/liter which represents a 129.4% concentration compared to saturation at the same temperature.

We have tried to determine the change in dielectric constant of the water enriched in carbon dioxide. The measuring arrangement shown in FIGS. 18 and 19 was, however, inappropriate to supply reliable results, since the presence of carbon dioxide increased the conductivity of the liquid and decreased the quality factor of the capacitance $C_x$.

The water enriched in carbon dioxide is a stable fluid, it has a sour taste resembling to that of club soda in which intensive bubble building can be experienced, the difference lies in that there is no bubble formation at all. The bonding of carbon dioxide to water occurs with substantially lower forces than in case of oxygen or air, if the water is shaked or stirred, the gas gets partly or wholly released.

The so-obtained water looses at least a part of its gas content with time i.e. in some days. We have filled plastic bags with water enriched with carbon dioxide and sealed the bags with an airtight seal. After some days the bags were collapsed as if they were exposed to an outer pressure or as if a vacuum would act from the interior. This can be explained by the fact that the specific volume of water comprising carbon dioxide is higher than that of water, and when the gas gets released from the water, the volume decreases and vacuum is established in the bottle effecting the intensive shrinking.

The stable presence of the gas introduced in water according to the present invention can be demonstrated by the various effects of such waters.

With the exception of carbon dioxide neither mixing, stirring, whipping could change the characteristic taste of the water.

In the following part of the specification examples will be described that demonstrate various uses and effects of the water which comprises specially bound gases, particularly oxygen provided by the method according to the invention. For the sake of simplicity, the water enriched in oxygen according to the present invention will be referred to as "oxygenized water".

EXAMPLE 1

Alcoholic beverage (brandy) was given to six persons. The alcohol amount in their blood was measured in an hour following the alcohol consumption. The average of the measured alcohol concentration was 1.3°/oo (varying between 1.25 and 1.38). The concentration was expressed as a quotient of consumed pure alcohol and of body weight multiplied by a distribution factor of 0.7 for men and 0.6 for women. In Switzerland this is the standard way of expressing alcohol concentration. The limit for driving is 0.8°/oo, furthermore if this value is higher than about 2° to 3,5°/oo, the person gets unconscious and the concentration above 4°/oo can be fatal.

When the samples were taken each person drank 1 dl of oxygenized water made with the apparatus shown in FIG. 1 from tap water. About 1½ hours later blood samples were taken again and the alcohol concentration of these blood samples was measured. The average of these measurements was 0.3°/oo of alcohol concentration with a very small deviation among the test persons.

After about half an hour following the consumption of oxygenized water the persons started to report that they felt better and the symptoms of alcoholic influence gradually vanished. By the time the blood samples were taken they all were sober and under full control.

It should be noted that the usual rate of decrease of alcohol concentration in blood is about 0.1°/oo per hour. If we compare this usual value with the result of this test, in which the rate of decrease was 1% in 1½ hours, then it can be seen that the presence of 1 dl oxygenized water results in about a seven times higher rate of alcohol metabolism in the human body.

EXAMPLE 2

Ten women were selected who suffered from candiditis due to the presence of *Candida albicans*. The ill areas were under the breast (at 6 persons), between the fingers (3 persons), at the genital and anal areas (3 persons).

The ill areas and their vicinity in an excess radius of two cm were smeared twice a day with oxygenized water during a period of two weeks. No other treatment was used.

The patients reported they were relieved from pain about after the third day of treatment. The skin areas were not yet healed by that time. The fastest healing was experienced under the breast areas. It took place by about the 7th day of treatment. The slowest healing was experienced between the fingers and at the tip of fingers. In that cases the healing occurred by the end of the tenth-twelfth day. Concerning the genital and anal areas healing was experienced after the tenth-thirteenth day.

All patients were examined a week and thereafter a month following the treatment. In the examination after one week there was a slight recurrence at a patient who had been treated between the fingers. The area turned to red again. The treatment was repeated for a further four days and the patient healed. In a control after a month she was healthy. In all other control examinations the patients were healed.

EXAMPLE 3

Seven male patients suffered from frostbite of first grade (congelatio curtis). The frostbitten areas were at the hands and feet and in one case at the ears.

The frostbitten areas were treated three times a day by sterilized tissues soaked previously in oxygenized water. The water was let to dry on the areas thereafter the wounds were bound by antiseptic gauze. No other treatment except for vitamins was applied.

The excessive pain started to decrease by the second or third day of treatment and stopped completely in further 3-5 days. The natural color of the skin returned rather soon and in all cases a complete healing took place by the tenth day of treatment.

EXAMPLE 4

Absorbent cotton was laid on a petri dish and 50 alfalfa seeds sown thereon. The absorbent cotton was fully soaked with oxygenized water. The wet condition of the cotton was maintained by discrete supply of oxygenized water. After about two days, when the rate of germination was inspected, it was found that 70% of the seeds had germinated. The rate of germination for a control where not oxygenized but normal water had been used was 50%. As a result, it was learned that soaking with oxygenized water led to a 20% higher germination rate. Further, when the rate of growth was observed after about five days, the average growth was found to be 28 mm, compared with an average 23 mm for the control group. In consideration of this it was learned that oxygenized water can be effective for promoting plant growth.

EXAMPLE 5

This example relates to the effect of water comprising carbon dioxide by means of the present invention. In the apparatus of FIGS. 1 to 3 the circulation process was maintained through 24 hours and the oxygen was replaced by carbon-dioxide. Absorbent cotton was laid on a petri dish and 50 alfalfa seeds there on. The absorbent cotton was fully soaked with the water comprising carbon dioxide. The wet condition of the cotton was maintained by discrete supply of water including carbon dioxide. After about two days, when the rate of germination was inspected, it was found that 50% of the seeds had germinated which was not different from the rate of 50% for normal water. When the rate of growth was observed after about five days, the average growth was found to be 25 mm compared with an average of 21 mm for the control group with normal water under the same conditions. From these results it was learned that water containing carbon dioxide according to the invention can also be effective for promoting plant growth.

The above examples can demonstrate that the water comprising excess amount of gases in bound state, especially oxygen, air and carbon dioxide has many different fields of applications and the results in these fields are surprisingly significant. There can be, of course, much more fields of applications and numerous beneficial effects.

In connection with such direct applications the question might be raised whether an overdosage of oxygenized water can be possible at all. In human organization there exists a regulation system which impedes that haemoglobin can take more oxygen than required even if oxygen is presented through the intestinal membrane in excess quantity. Excess oxygen can be dangerous when breathed in through the lungs only.

It is claimed:

1. Apparatus for introducing gas into water, comprising a container (1, 34) storing said water and having a space above water filled with gas to be introduced, a closed path of conduits (16, 17, 18) starting from and ending in said container, a pump (14) inserted in said path to recirculate water in said path, characterized in that a reaction chamber (15) is connected in said path, the reaction chamber (15) has an inner space with a rotational symmetrical form that has an axis, a plurality of tangential inflow openings (24) are provided near inflow end of said inner space to cause rotation of inflowing water around said axis, in the path of rotating flow of water in front of the openings (24) the reaction chamber (15) has a part (26) with continuously tapering cross section ending in a short duct (27), said path has a widening portion in front of the duct (27), and said closed path comprises means for intensively contacting said gas with said water.

2. The apparatus as claimed in claim 1, wherein said gas space in the container communicating with a gas supply means for supplying measurable quantity of gas in said space, in operation said means providing atmospheric pressure in said space.

3. The apparatus as claimed in claim 1, wherein said reaction chamber (15) has an inflow end portion (23) with a hollow rotational paraboloid form, said openings (24) are defined in the wall of said inflow end portion (23), an inflow duct (25) is coupled to said path and a cylindrical pressure chamber is formed between said duct (25) and outer wall of said paraboloid portion (23).

4. The apparatus as claimed in claim 1, comprising means (31) for condensing vapor from said gas space.

5. The apparatus as claimed in claim 1, comprising temperature regulator means (30) for adjusting the temperature of circulating water to a preset value.

6. The apparatus as claimed in claim 1, wherein said means for contacting the gas with water is a water jet pump (35) with water inflow and outflow ducts connected in series in said path and a gas inlet duct (45) connected with said gas space of said container (1, 34).

7. The apparatus as claimed in claim 6, wherein a plurality of reaction chambers (15a, 15b, 15c) are connected in parallel across said path.

8. The apparatus as claimed in claim 1, wherein said means for contacting the gas with water is formed by said container (1) that defines an inner space being circularly symmetrical relative to an axis (5), said container (1) has an upper part (2) with a substantially spherical shape, a medium part (3) tapering in a direction away from the upper part (2) and a narrow lower part (4) tapering in the same direction and ending in an outflow opening, a duct (13) is extending obliquely out of the upper portion of the medium part (2) substantially at or just below a height in which the container (1) has the largest diameter and closes an acute angle at least with the tangential plane of the container for introducing water and for forming a vortex in said container, said duct (13) and said outflow opening are coupled to said closed path.

9. The apparatus as claimed in claim 8, wherein a plurality of reaction chambers (15a, 15b, 15c) are connected in parallel across said path.

* * * * *